United States Patent [19]

Sutherland

[11] Patent Number: 4,684,508

[45] Date of Patent: Aug. 4, 1987

[54] BLOOD HEAT EXCHANGER

[75] Inventor: Karl M. Sutherland, Westminster, Calif.

[73] Assignee: American Hospital Supply Corp., Evanston, Ill.

[21] Appl. No.: 860,710

[22] Filed: May 5, 1986

Related U.S. Application Data

[63] Continuation of Ser. No. 565,236, Dec. 27, 1983, abandoned.

[51] Int. Cl.⁴ .......................... A61M 1/14; F28D 3/02; F28F 1/14; F28F 1/36
[52] U.S. Cl. .......................... 422/46; 422/47; 128/DIG. 3; 261/DIG. 28; 165/163; 165/184
[58] Field of Search ............. 422/46, 47; 128/DIG. 3; 261/DIG. 28; 165/163, 184

[56] References Cited

U.S. PATENT DOCUMENTS

| 4,138,464 | 2/1979 | Lewin | 422/46 |
| 4,268,476 | 5/1981 | Raible | 422/47 |
| 4,282,180 | 8/1981 | Raible | 422/46 |
| 4,336,224 | 6/1982 | Siposs | 422/47 |
| 4,374,088 | 2/1983 | Stenberg et al. | 422/46 |
| 4,440,723 | 4/1984 | Gordon | 422/47 |

Primary Examiner—Michael S. Marcus
Assistant Examiner—Lynn M. Kummert

[57] ABSTRACT

An improved structure for directing the flow of blood and blood foam onto a heat exchanger in a bubble blood oxygenator is disclosed. An extended skirt extends from the plate where venous blood and oxygen are mixed to the top of the heat exchanger of the blood oxygenator. Blood and blood foam flow downwardly uniformly over the mixing plate and evenly onto the heat exchanger. Full utilization of the heat exchanger may thereby be more easily achieved.

9 Claims, 3 Drawing Figures

BLOOD HEAT EXCHANGER

This is a continuation of application Ser. No. 565,236, filed Dec. 27, 1983, now abandoned.

BACKGROUND OF THE INVENTION

The invention herein relates to bubble-blood oxygenators of the type used in thoracic surgery, and more particularly to an improved means for directing the flow of blood and blood foam onto the heat exchanger of such oxygenators. The present invention is an improvement upon and useful in connection with the devices shown in Bentley U.S. Pat. No. 4,282,180 issued Aug. 4, 1981, entitled "Blood Oxygenator".

The history of safe and reliable blood oxygenators is relatively brief. Such oxygenators are used in open-heart surgery and other operations and treatments of the body when it is necessary to establish an extracorporeal circulation system for temporarily assuming the function of the heart and lungs of the patient. In such a system, the oxygenator operates to perform the function usually performed by the lungs of the patient, i.e. the life supporting transfer of oxygen into the blood and the carbon dioxide out of the blood. In addition to gas transfer, the oxygenator serves to cool or heat the extracorporeal blood. Cooling the blood cools the patient which resultantly reduces the oxygen requirements of the patient. Since less oxygenation is required, the volume of extracorporeal blood needed to be oxygenated is less.

Oxygenators which both oxygenate the blood and regulate its temperature have been well known. Such oxygenators of the bubble-blood type operate by mixing oxygen deficient, i.e. venous, blood with oxygen to produce blood foam. The blood and blood foam is then flowed over a heat exchanger element and into a defoaming stage where the oxygenated, temperature regulated blood is stored for use in the patient.

The mixing of the venous blood with the oxygen will typically occur in some form of mixing chamber. For example, in an early bubble blood oxygenator containing an integral heat exchanger, designed by Dr. Frank Gollan in the 1950's and published in his book *The Physiology of Cardiac Surgery, Hypothermia, Extracorporeal Circulation and Extracorporeal Cooling*, the blood foam is produced by forcing oxygen through a sparger plate of sintered glass into the lower portion of the bubble column into which the venous blood is introduced. The blood foam then flows up the bubble column, over the heat exchanger section and into a defoamer section. No attempt was made to preferentially direct the blood foam onto the heat exchanger section.

Currently available bubble blood oxygenators do not specifically attempt to direct the flow of blood foam onto the heat exchanger section. The blood oxygenator described in Bentley U.S. Pat. No. 4,282,180 utilizes a blood-oxygen mixing area and an integral heat exchanger. Considering in more detail the blood-oxygen mixing area of the oxygenator described in Bentley U.S. Pat. No. 4,282,180, incorporated herein by reference, as schematically shown in FIG. 1, the venous blood is introduced into an annular chamber 14 in a generally tangential manner. As the blood circles in the annular chamber 14, oxygen gas is introduced in bubble form into the chamber through a diffusion means 13 in the chamber bottom. The blood and oxygen bubbles form blood foam which passes from the annular chamber through a distribution channel 16, over a mixing plate 20, and into a mixing chamber 17 which contains the heat exchanger 18.

The preferred heat exchanger design consists of a helically coiled, ribbed heat exchanger conduit over which the blood and blood foam is flowed. Since the conduit shape is a helical spiral the upper end of the conduit is necessarily closer to the top of the oxygenator than is a portion of the conduit which is further down the helix. Accordingly, the gap between the distribution channel and the heat exchange coil increases as one proceeds down the helix of the conduit. No preferential direction is imparted to the blood foam leaving the distribution channel.

Blood and blood foam have a fairly high degree of surface tension which sometimes causes undirected or unconstrained blood to flow together. As a result, blood and blood foam may occasionally flow over the mixing plate and onto the heat exchange conduit unevenly, more flowing onto one portion of the coil than another.

SUMMARY OF THE INVENTION

In the present invention fuller utilization of the heat exchanger is achieved by providing a path from the bloodoxygen mixing area to the helically wound conduit. This path may consist of an extended skirt which extends from the mixing area to the conduit. The skirt length extends in a helical fashion in order to track the spiral of the helically wound conduit. The skirt is preferably in contact with the coil, though effective utilization of the heat exchanger may be achieved if the gap between the skirt and the coil is small enough to allow uninterrupted flow across it.

The extended skirt reduces the possibility of the blood and blood foam flowing together, thereby resulting in a more even distribution of the blood and blood foam over the mixing plate and the heat exchanger. The higher utilization of the heat exchanger results in more effective heat transfer with the possible utilization of reduced extracorporeal blood volume.

The extended skirt arrangement additionally directs the blood and blood foam more directly to the heat exchange conduit. Blood oxygenators which flow the blood and blood foam down over the heat exchange conduit will operate effectively even if the heat exchange conduit is not in contact with or closely proximate to the inner wall of the mixing chamber 17 containing the heat exchanger. In such a case the blood and blood foam is advantageously directed to the heat exchange coil and away from the wall. Blood and blood foam which flow down the wall bypass the heat exchange conduit and thereby avoid the important temperature regulation aspect of these blood oxygenators. The extended skirt arrangement directs the flow of blood and blood foam to the heat exchange coil and away from the wall, resulting in fuller utilization of the heat exchange conduit.

It is an object of this invention to provide an improved method of distributing blood and blood foam on a heat exchange conduit in a bubble-blood oxygenator.

It is a further object of this invention to provide an improved means of directing blood and blood foam onto a heat exchange conduit and away from the inner wall of the mixing chamber.

It is a further object of this invention to provide for more effective utilization of the heat exchange in a bubble-blood oxygenator.

Further objects of this invention will become apparent to those skilled in the field from the following description and drawings.

BRIEF DESCRIPTION OF THE DRAWINGS

A more thorough disclosure of the objects and advantages of the present invention are presented in the detailed description which follows and from the accompanying drawings of which

DETAILED DESCRIPTION

The Bentley BOS Series oxygenators have proven to be safe, highly effective blood oxygenators. In an effort to improve upon this high level of performance the invention disclosed herein has been devised. This invention is more fully appreciated when the current BOS oxygenators is understood.

Figure 1:
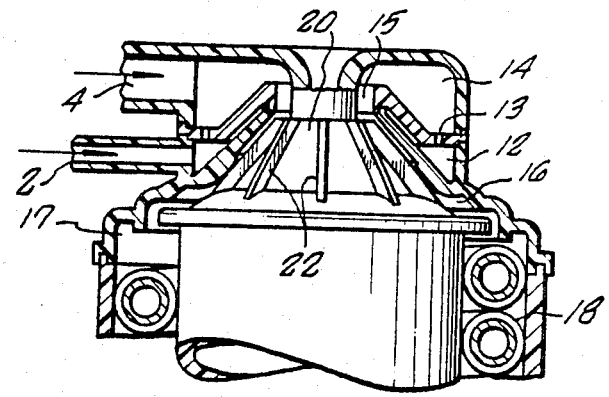
FIG. 1 is a schematic drawing of the unmodified interface between the blood mixing area and the heat exchange coil.

The general structure disclosed in Bentley U.S. Pat. No. 4,282,180 is shown in FIG. 1. The upper portion of the oxygenator generally serves to admix the venous blood and oxygen in order to produce blood foam. The blood foam is then passed on to the heat exchanger where gas transfer and heat exchange occur.

Structurally, oxygen gas is introduced into an annular chamber 12 through gas inlet 2, the annular chamber 12 having a diffusion means 13 typically in the form of a plurality of holes allowing the oxygen gas to escape. Venous blood is introduced into an annular chamber 14 through a blood inlet or inlets 4. Oxygen gas bubbles from the annular chamber 12 through the diffusion means 13 and into the venous blood contained in the annular chamber 14. Blood foam flows across a mixing plate 20 which forms one wall of the distribution channel 16. Spacer ribs 22 may be used to space the mixing plate 20 away from the underside of the annular chamber 12 which defines the other wall of the distribution channel 16.

The downstream end of the distribution channel 16 typically terminates at a uniform height at the top of the annular mixing channel 17 irrespective of the relationship of the end of the distribution channel to the heat exchanger tube 18. The heat exchange tube 18, however, is generally helically coiled, spiraling down the annular mixing chamber 17. As a result, the upper coil of the heat exchange tube 18 is progressively further away from the end of the distribution channel 16. The gap between the end of the distribution channel 16 and the first coil of the heat exchanger tube 18 varies between 1/16 inches at a minimum to 158 inches after one complete rotation.

In operation, the blood foam will flow over the mixing plate 20 and through the distribution channel 16 and onto the heat exchange tube 18. The surface tension of the blood and blood foam may cause the blood foam to draw together and flow unevenly over the surface of the mixing plate. The blood and blood foam arriving at the end of the distribution channel 16 will then flow over to the heat exchange coil 18 in an uneven fashion, reflecting the uneven distribution on the mixing plate 20.

The efficient utilization of the heat exchange coil 18 may be accomplished by providing an extended skirt 30 extending from the mixing plate 20. Providing the extended skirt 30 reduces the tendency of the blood foam to flow together and preferentially flow over the mixing plate 20. As a result, the blood foam flows onto the heat exchange coil 18 more uniformly and, accordingly, utilizes a larger fraction of the heat exchange coil 18.

Figure 2:
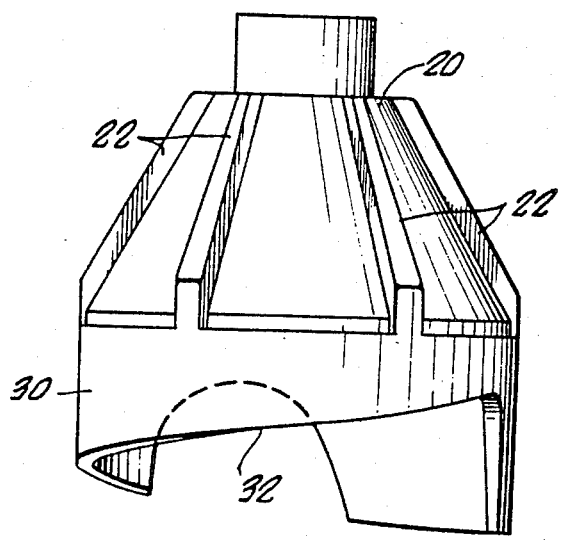
FIG. 2 is an elevation view of the extended skirt and mixing plate.

The extended skirt 30 is shown in relation to the mixing plate 20 in FIG. 2. As shown, the extended skirt 30 and mixing plate may be manufactured as a continuous piece, as for example, out of one piece of polycarbonate. The extended skirt 30 generally will extend in a vertical direction, though the direction is not critical. The lower edge 32 of the extended skirt 30 should be designed so as to generally track the shape of the uppermost coil of the heat exchange coil 18. Typically the edge 32 will be inclined so as to follow the spiral of the heat exchange coil 18. Additionally, provision may be made for an inlet or outlet of the heat exchange conduit should the coil be so designed.

Figure 3:
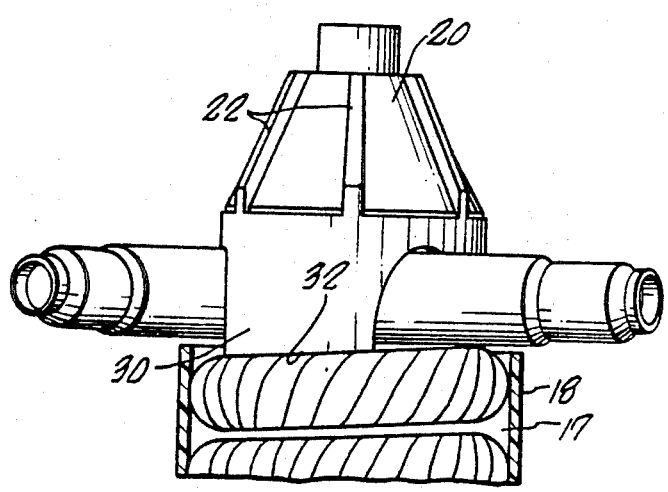
FIG. 3 shows the mixing plate and extended skirt in an operating relationship with the heat exchanger.

It has been found that optimal results are obtained when the lower edge 32 of the extended skirt 30 is in contact with the heat exchange tube 18. FIG. 3 shows an extended skirt in such relationship to a heat exchange tube. In this way an uninterrupted pathway exists for the blood and blood foam to flow from the mixing plate to the heat exchange tube 18 without substantial interruption. The gap between the lower edge 32 of the extended skirt 30 and the heat exchange tube 18 need not be eliminated. The advantages of this invention are achieved even if there is no gap. The gap should be small enough that the blood and blood foam do not tend to draw together on the mixing plate and extended skirt 30.

The positioning of the extended skirt 30 in relation to other elements of the blood oxygenator is determined by the type of blood oxygenator utilizing this invention. Some blood oxygenators, such as the Bentley BOS-10, flow the blood and blood foam gently down over the heat exchanger coil 18. Ideally the blood and blood foam flow down over the coils and do not flow over to the inner wall of the annular mixing chamber 17, thereby avoiding the heat exchange coil. The extended skirt arrangement helps to insure that the blood and blood foam are directed completely onto the heat exchange coil, and reduces the tendency of the blood and blood foam to flow out of the distribution channel and onto the inner wall of the mixing chamber.

The advantages of this invention are achieved even if the heat exchange coil 18 is in contact with or closely proximate to the inner wall of the mixing chamber 17. The blood and blood foam may be uniformly distributed onto the heat exchange coil thereby achieving fuller utilization of the heat exchange coil.

Certain blood oxygenators flow the blood and blood foam up through the annular mixing chamber 17. This invention may be employed advantageously in such an oxygenator to achieve more uniform distribution of the blood and blood foam over the heat exchanger coil. The extended skirt extends from the bloodoxygen mixing area to the bottom of the heat exchange coil. The blood and blood foam are thus preferentially directed to the heat exchanger coil.

What is claimed is:

1. In a blood oxygenator having an elongated housing, a blood and oxygen mixing area disposed at one end of said housing, a blood inlet means and oxygen inlet means connected to and communicating with said blood and oxygen mixing area, an annular mixing chamber disposed along at least a portion of said housing, and a helical heat exchanger conduit including a plurality of turns disposed in said annular mixing chamber, the improvement comprising:

a mixing plate disposed in said blood and oxygen mixing area and means connected to a lower portion of said mixing plate for directing blood foam downwardly from the mixing plate to said heat exchanger conduit;

wherein said directing means comprises a skirt extending downwardly from said mixing plate and terminating in an edge disposed proximate to said helical heat exchanger conduit, said edge being substantially helical in shape along at least a portion thereof so that said edge of said skirt extends proximate to an uppermost turn of said heat exchanger conduit along a helical portion of such turn.

2. The blood oxygenator of claim 1, wherein said edge of said skirt is substantially in contact with said helical heat exchanger conduit.

3. The blood oxygenator of claim 1, wherein said mixing plate is generally conical in shape and includes a plurality of ribs on its upper surface.

4. The blood oxygenator of claim 3, wherein said edge of said skirt is substantially in contact with said helical heat exchanger conduit.

5. The blood oxygenator of claim 4, wherein said mixing plate and said skirt are one-piece.

6. A heat exchanger for use in a blood oxygenator comprising:

a helical heat exchanger conduit having an uppermost winding;

a generally conical mixing plate and an extended skirt depending from the mixing plate and terminating in an edge which is substanially helical over at least a portion of such edge and which confronts an upper winding of the heat exchanger conduit closely adjacent thereto; and means for directing a blood-oxygen mixture onto the mixing plate for downward flow over the heat exchanger conduit.

7. A heat exchanger as described in claim 6 wherein the helical portion of said edge of the skirt tracks the uppermost winding of the heat exchanger conduit.

8. The improved heat exchanger of claim 6 wherein the mixing plate and extended skirt are one-piece.

9. The improved heat exchanger of claim 8 wherein the one-piece mixing plate and skirt are of polycarbonate material.

* * * * *